(12) United States Patent
Hamilton et al.

(10) Patent No.: US 11,692,997 B2
(45) Date of Patent: *Jul. 4, 2023

(54) BREATH TESTING APPARATUS

(71) Applicant: QUINTRON INSTRUMENT COMPANY, INC., Milwaukee, WI (US)

(72) Inventors: Eric Lyle Hamilton, New Berlin, WI (US); Katherine Ross, West Allis, WI (US)

(73) Assignee: QuinTron Instrument Company, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/542,928

(22) Filed: Dec. 6, 2021

(65) Prior Publication Data

US 2022/0091098 A1    Mar. 24, 2022

Related U.S. Application Data

(63) Continuation of application No. 16/818,267, filed on Mar. 13, 2020, now Pat. No. 11,193,926.

(51) Int. Cl.
*G01N 33/497*    (2006.01)
*A61B 5/08*    (2006.01)
*A61B 5/097*    (2006.01)

(52) U.S. Cl.
CPC .......... *G01N 33/497* (2013.01); *A61B 5/082* (2013.01); *A61B 5/097* (2013.01); *G01N 2033/4975* (2013.01)

(58) Field of Classification Search
CPC .......... G01N 33/497; G01N 2033/4977; A61B 5/082; A61B 5/083; A61B 5/097
See application file for complete search history.

(56) References Cited

U.S. PATENT DOCUMENTS

| | | | |
|---|---|---|---|
| 5,425,374 | A | 6/1995 | Ueda et al. |
| 9,289,714 | B1 | 3/2016 | Juvan |
| 9,341,576 | B2 | 5/2016 | Acharya et al. |
| 9,357,946 | B2 | 6/2016 | Johnson et al. |

(Continued)

FOREIGN PATENT DOCUMENTS

| | | |
|---|---|---|
| EP | 2809425 | 12/2014 |
| EP | 3015165 | 5/2016 |

(Continued)

OTHER PUBLICATIONS

International Search Report dated Feb. 26, 2021 from PCT/US2020/055702 filed Oct. 15, 2020; 3 pgs.

(Continued)

*Primary Examiner* — Herbert K Roberts
(74) *Attorney, Agent, or Firm* — Ryan Kromholz & Manion, S.C.

(57) ABSTRACT

A breath testing apparatus is provided to test hydrogen sulfide and other parameters in exhaled breath of a patient. A patient sample input for receiving exhaled breath from a patient is provided, in addition to an atmospheric input for receiving atmospheric air. A valve is coupled to said patient sample input and said atmospheric input, and first and second pathways are provided from said valve to a hydrogen sulfide sensor block and a second sensor block.

6 Claims, 3 Drawing Sheets

(56) References Cited

U.S. PATENT DOCUMENTS

| | | |
|---|---|---|
| 9,358,276 B2 | 6/2016 | Lin et al. |
| 2005/0065446 A1 | 3/2005 | Talton |
| 2006/0196507 A1 | 9/2006 | Bradley |
| 2010/0081955 A1* | 4/2010 | Wood, Jr ............... A61B 5/097 |
| | | 600/532 |
| 2011/0021942 A1* | 1/2011 | Choe ..................... A61B 5/097 |
| | | 600/532 |
| 2015/0032019 A1* | 1/2015 | Acker ................... A61B 5/097 |
| | | 600/532 |
| 2015/0250408 A1* | 9/2015 | Ssenyange ........ G01N 33/0037 |
| | | 600/532 |
| 2015/0335267 A1 | 11/2015 | Cormier et al. |
| 2016/0018371 A1 | 1/2016 | Acharya et al. |
| 2016/0058779 A1 | 3/2016 | Casola et al. |
| 2016/0077047 A1 | 3/2016 | Khamis et al. |
| 2016/0077069 A1 | 3/2016 | Kim et al. |
| 2016/0122698 A1 | 5/2016 | Suslick et al. |
| 2016/0150995 A1 | 6/2016 | Ratto et al. |
| 2016/0153964 A1 | 6/2016 | Donnay |
| 2018/0271404 A1 | 9/2018 | Gupta |
| 2020/0064330 A1 | 2/2020 | Pimentel |

FOREIGN PATENT DOCUMENTS

| | | | |
|---|---|---|---|
| ES | 2731549 | 11/2019 | |
| ES | 2731549 A1 * | 11/2019 | ............. A61B 5/082 |
| ES | 2731549 A1 | 11/2019 | |
| WO | WO2015/002880 | 1/2015 | |
| WO | WO2016/036956 | 3/2016 | |
| WO | WO2016/085824 | 6/2016 | |

OTHER PUBLICATIONS

Written Opinion dated Feb. 26, 2021 from PCT/US2020/055702 filed Oct. 15, 2020; 5 pgs.

* cited by examiner

BREATH TESTING APPARATUS

RELATED APPLICATIONS

This application is a continuation of co-pending application Ser. No. 16/818,267, filed 13 Mar. 2020.

BACKGROUND OF THE INVENTION

This invention relates to the field of sampling air from the lungs and specifically to the field of obtaining a sample of a person's air, including alveolar air from the alveoli of the lungs of a person.

Air from the lungs of a person can be used for many different types of testing that would otherwise require the person to undergo an invasive procedure. For example, alveolar air can be analyzed for, but not limited to, the noninvasive diagnosis of a wide variety of conditions including the noninvasive diagnosis of stomach infections related to a high incidence of ulcers, enzymatic deficiencies, and metabolic conditions and/or abnormalities. Crucial to any such testing is the ability to get an accurate sample containing a sufficient volume of air representative of true alveolar air, necessary for specific testing.

Hydrogen and methane are produced in the digestive system primarily only by the bacterial fermentation of carbohydrates (sugars, starches or vegetable fibers), so either of these gases appear in the expired air, it is usually a signal that carbohydrates or carbohydrate fragments have been exposed to bacteria, permitting such fermentation to take place. Levitt, M. D. Production and excretion of hydrogen gas in man. New Engl. J. Med 1968; 281:122 (incorporated herein by reference). The generation of H2 and/or CH4 will result in the reabsorption of some of these gases into the blood stream from the site of their digestion, and they will appear in the expired air.

Bacteria are ordinarily not present in significant numbers in the small intestine, where digestion and absorption of sugars take place. Therefore, when a challenge dose (eg. lactose) is ingested, the level of hydrogen in alveolar air will rise significantly within one to two hours (depending on the intestinal transit time) only if the sugar is not digested and, therefore reaches the colon.

The breath-H2 test is a simple non-invasive procedure which is readily accepted by patients and staff (Metz, G.; Jenkins, D. L.; Peters, T. J,; Newman, A.; Blendis, L. M. Breath hydrogen as a diagnostic method for hypolactasia. Lancet. 1975; 1(7917):1155-7, incorporated herein by reference), and which has greater reliability and acceptability than the blood test, according to most reports in the literature (DiPalma, J. A.; Narvaez, R. M. Prediction of lactose malabsorption in referral patients. Dig Dis Sci. 1988; 33:303, incorporated herein by reference, and Davidson, G. P.; Robb, T. A. Value of breath hydrogen analysis in management of diarrheal illness in childhood: Comparison with duodenal biopsy. J Ped Gastroenterol Nutr. 1985; 4:381-7; Fernandes, J.; Vos, C. E.; Douwes, A, C,; Slctema, E.; Degenhart, H. J. Respiratory hydrogen excretion as a parameter for lactose malabsorption in children. Amer J Clin Nutr. 1978; 31:597-602; Newcomer, A. D.; McGill, D. B.; Thomas, R. J.; Hofmann, A. F. Prospective comparison of indirect methods for detecting lactase deficiency. New Engl J Med. 1975; 293:1232-6; Douwes, A. C.; Fernandes, J.; Degenhart H. J. Improved accuracy of lactose tolerance test in children, using expired H2 measurement. Arch Dis Child. 1978; 53:939-42; Solomons, N. W.; Garcia-Ibanez, R.; Viteri, F. E. Hydrogen breath test of lactose absorption in adults: The application of physiological doses and whole cow's milk sources. Amer J Clin Nutr. 1980; 33:545-54; each incorporated by reference).

The lower dose of lactose usually does not cause the discomfort and explosive diarrhea frequently seen by malabsorbers who are given the large dose required for the blood test.

A study with over 300 patients showed that G-I symptoms after a lactose challenge are strongly associated with the amount of H2 excreted, and the relationship between blood glucose change and symptom-severity was less evident. Jones, D. V.; Latham, M. C.; Kosikowski, F. V.; Woodward, G. Symptom response to lactosereduced milk in lactose-intolerant adults. Amer J Clin Nutr. 1976; 29(6):633-8, incorporated by reference.

False-positive breath-tests are rare, and when they occur they are usually caused by improperly doing the test—allowing the subject to smoke, to sleep or to eat shortly before or during the test11. Bacterial overgrowth (from the colon retrograde into the small intestine) can also produce a false-positive breath-test, but it is usually preceded by an elevated fasting breath-H2 level and the response is seen soon after the sugar is ingested (within 20-30 minutes).

The incidence of false-negative results with the breath-test is well below that seen with the blood test. False-negative results are reported to be from 5-15% of all lactose malabsorbers. Filali, A.; Ben Hassine, L.; Dhouib, H.; Matri, S.; Ben Ammar, A.; Garoui, H. Study of malabsorption of lactose by the hydrogen breath test in a population of 70 Tunisian adults. Gastroenterol Clin Biol. 1987; 11:554-7; Douwes, A. C.; Schaap, C.; van der Kleivan Moorsel, J. M. Hydrogen breath test in school children. Arch Dis Child. 1985; 60:333-7; Rogerro, P.; Offredi, M. L.; Mosca, F.; Perazzani, M.; Mangiaterra, V.; Ghislanzoni, P.; Marenghi, L.; Careddu, P. Lactose absorption and malabsorption in healthy Italian children: Do the quantity of malabsorbed sugar and the small bowel transit time play roles in symptom production? J Pediatr Gastroenterol Nutr. 1985 (February); 4(1):82-614; each incorporated by reference. This is due to a variety of causes. Many of the false-negative reports can be avoided by measuring methane in addition to hydrogen because some methanogenic flora convert colonic H2 to CH4. Cloarac, D.; Bornet, F.; Gouilloud, S.; Barry, J. Ll.; Salim, B.; Galmiche, J. P. Breath hydrogen response to lactulose in healthy subjects: relationship to methane producing status. Gut. 1990 (March); 31:300-4; incorporated by reference.

SUMMARY OF THE INVENTION

In accordance with the present invention, a testing apparatus is provided. A breath collection apparatus is used to collect a patient breath sample.

The patient breath sample is transported through a patient dessication unit by a sample pump, to a humidity sensor, and a flow sensor. At a first valve, a portion of the sample is discharged to the atmosphere, and the remainder of the sample is transported to a second valve at a patient sample input. At the second valve, an atmospheric input also is introduced. The atmospheric input receives air from the atmosphere by a pump that delivers the atmospheric input through in sequence, a room dessicant unit, a humidity sensor, a variable airflow valve, a flow sensor, and last an atmospheric air valve, which provides the atmospheric air into the second valve, as well as discharging excess back into the atmosphere.

From the second valve, the patient sample/atmospheric air combination passes to a t-valve which divides the patient sample/atmospheric air combination into two pathways. The first pathway leads to a hydrogen sulfide block, and the second pathway leads to a second sensor block.

The system is coupled to a computer/display unit at selected locations via connections preferably between for example the computer/display unit and: sample pumps, humidity sensors, flow sensors, valves, the hydrogen sulfide sensor block and the second sensor block.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
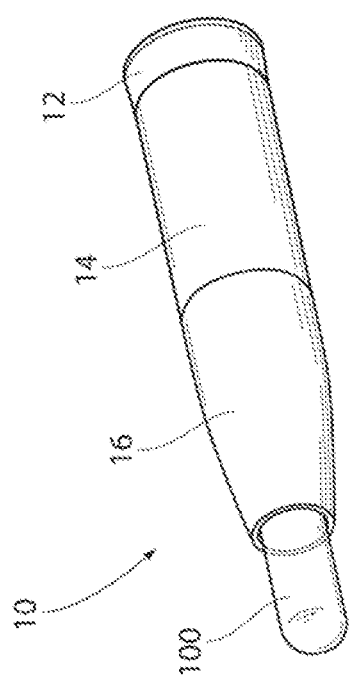
FIG. 1 is a perspective view of a sample collection apparatus, with an evacuated air chamber inserted into a distal end of a discharge chute.

Referring now to FIG. 1 a perspective view of a sample collection apparatus 10 of the present invention is shown. A mouthpiece 12 comprising a breath entryway is shown, to allow breath to pass to collection chamber 14. A breath discharge chute 16 receives an evacuated air chamber 100 that receives an end-expiration breath sample (described later) from within the collection chamber 14.

Figure 2:
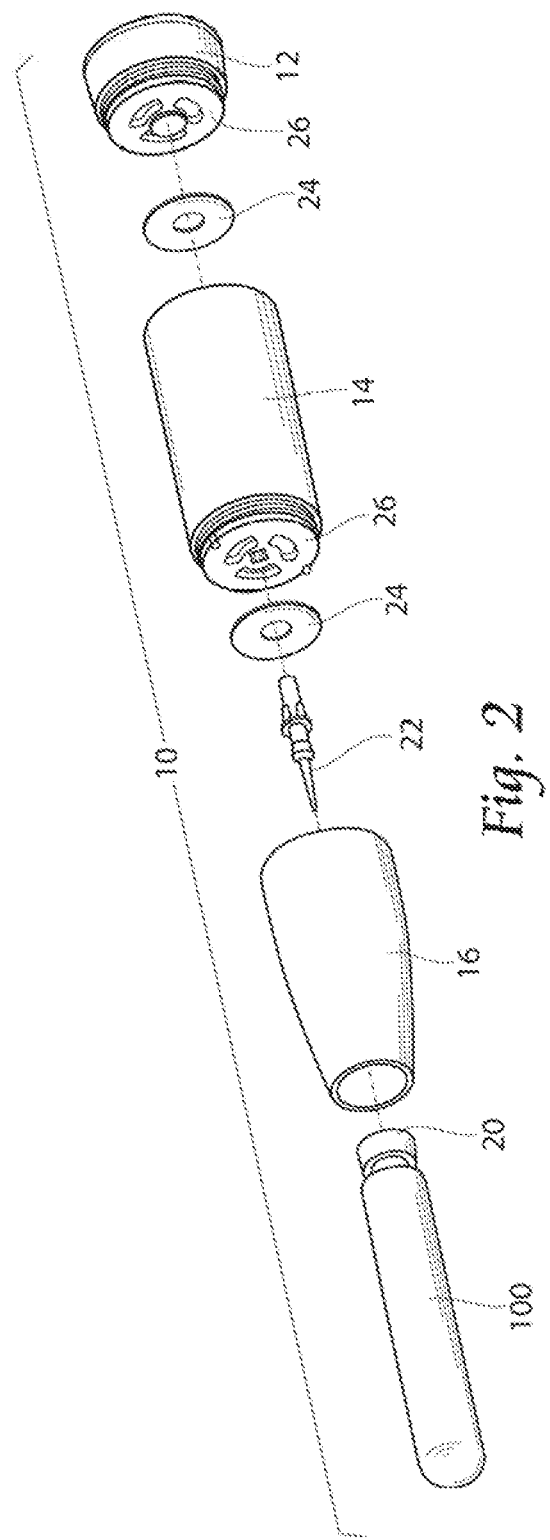
FIG. 2 is an exploded perspective view of a sample collection apparatus.

Referring now to FIG. 2, an exploded perspective view of a sample collection apparatus 10 of the present invention is shown. Mouthpiece 12 is either integrally formed or coupled with a one-way discharge assembly 26. Positive pressure from a breath, through the mouthpiece 12, causes flexible ring 24 to flex, and allow air to pass into collection chamber 14 at an upstream end of collection chamber 14. Flexible ring 24, is preferably, but not necessarily, a flutter valve. Another one-way discharge structure 24, again coupled to a flexible ring 24 (and again preferably, but not necessarily, a flutter valve), is coupled to a downstream end of collection chamber 14. Coupled to the interior of collection chamber 14 is discharge needle 22, which provides a selective passageway from breath between collection chamber 14 and ultimately evacuated air chamber 100, which is coupled to discharge needle 22 through discharge chute 16.

Figure 3:
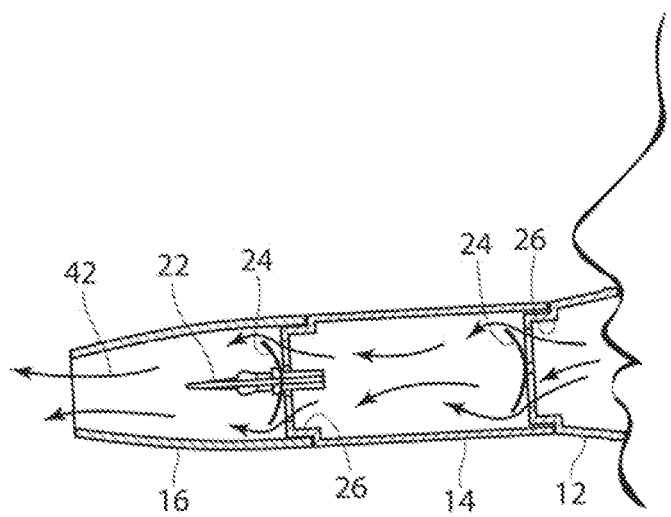
FIG. 3 is an in-use side cross-sectional view of a sample collection apparatus, shown collecting a breath sample.

Referring now to FIG. 3, an in-use side cross-sectional view of sample collection apparatus 10 is shown. A patient has pressed a mouth to mouthpiece 12 and began exhalation. The first volume of breath 42 evacuates background air from within collection 14, and first volume of breath 42, being not the most desirable for alveolar air sampling, is expelled through discharge chute 16 without capture. Positive pressure from the breath sample flexes flexible rings 24, allowing air to continue to flow through collection chamber 14, into discharge chute 16.

As the breath stops, the positive pressure from the breathing stops as well, allowing flexible rings 24 to return to their static position, flush against one-way discharge structures 26 at the upstream and downstream ends of collection chamber 14. As the flexible rings 24 seal the collection chamber 14, end-expiration breath sample 40 is captured in collection chamber 14. To retrieve the end-expiration breath sample 40 for convenient sampling by gas chromatography equipment, it is desirable to collect end-expiration breath sample 40 in an evacuated air chamber 100 (a test tube). Evacuated air chamber 100 is of a volume V1, which is preferably a smaller volume than volume V2 of the collection chamber 14, so that evacuated air chamber 100 collects only end-expiration breath sample 40 from the collection chamber 14, and not outside air drawn through collection chamber 14.

Figure 4:
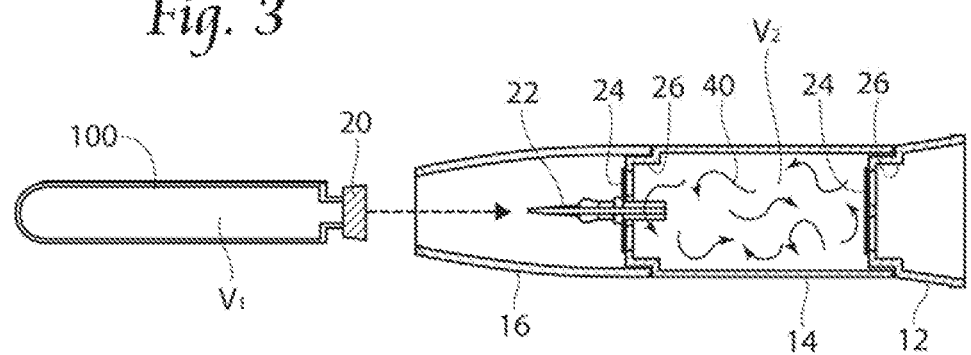
FIG. 4 is a side cross-sectional view of a sample collection apparatus, with an evacuated air chamber being inserted into a distal end of the discharge chute.
Figure 5:
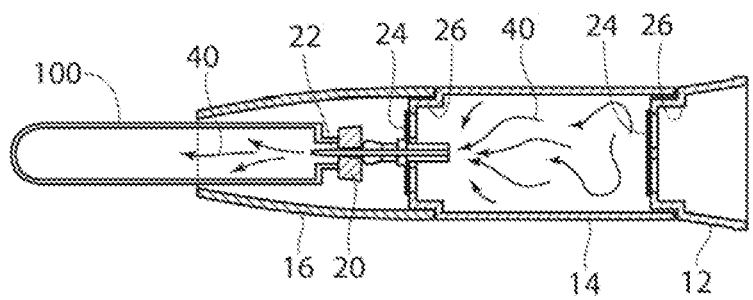
FIG. 5 is a side cross-sectional view of a sample collection apparatus, with an evacuated air chamber being inserted onto a discharge needle within the discharge chute.
Figure 6:
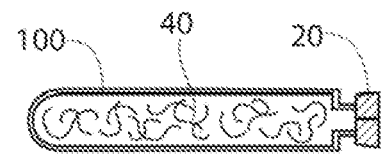
FIG. 6 shows a collected an end-expiration breath sample.

Evacuated air chamber 100 is inserted into a distal end of the discharge chute 16 as shown in FIG. 4, and as shown in FIG. 5, evacuated air chamber 100 is inserted onto discharge needle 22, piercing a septum 20 (preferably self-sealing) of air chamber 100. The evacuated air chamber 100 then retrieves end-expiration breath sample 40 from collection chamber 14. After air chamber 100 has retrieved end-expiration breath sample 40 from collection chamber 14, the air chamber 100 can be withdrawn from the discharge needle 22 within discharge chute 16. Shown in FIG. 6, the air chamber 100 containing end-expiration breath sample 40 can then be processed in a laboratory for target analytes as desired.

Figure 7:
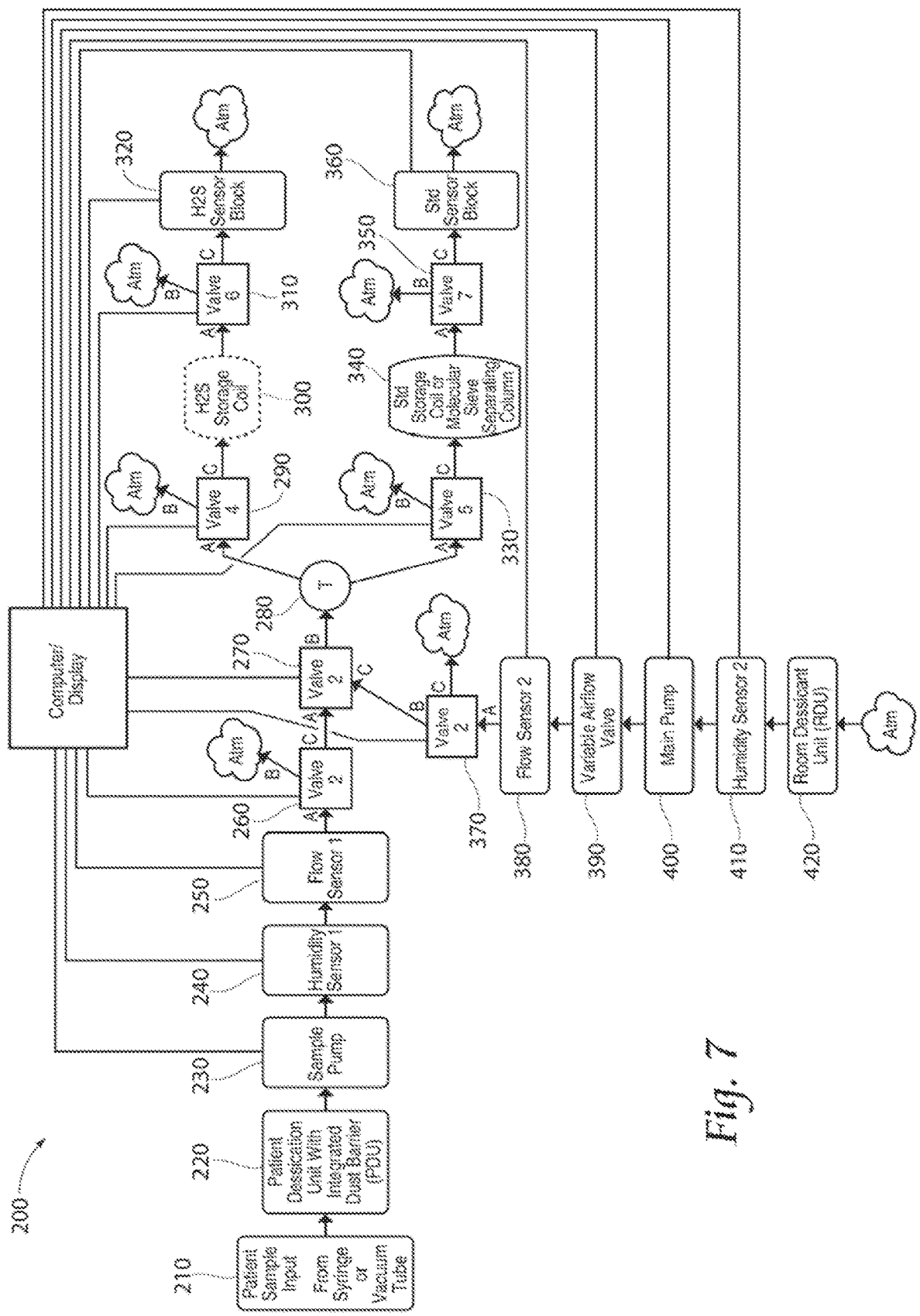
FIG. 7 is a schematic for an air sample unit of the present invention.

In a preferred embodiment, now referring now to FIG. 7, a schematic for an air sample unit 200 of the present invention is shown. The air chamber 100 containing end-expiration breath sample 40 can be hooked up a location 210 where the patient breath sample 210 is transported through a patient dessication unit 220, by sample pump 230, a humidity sensor 240, and a flow sensor 250. Instead of a traditional dessicant unit 220 alternative drying can be used such as Nafion™ tubing. At a first valve 260, a portion of the sample 210 is discharged to the atmosphere, and the remainder of the sample is transported to a second valve 270 at a patient sample input C/A.

At the second valve 270, an atmospheric input also is introduced. In a preferred embodiment, sensors 320 and 360 receive constant dehumidified air on them for test and operational stability if sample air is not being tested. Sensor block 360 preferably comprises at least one of hydrogen, methane, and carbon dioxide sensors. In this preferred embodiment, when a patient sample is introduced in input 210, room dessicant unit 420 air is interrupted, and patient sample is introduced in input 210. The atmospheric input at 270 receives air from the atmosphere through, in sequence, a room dessicant unit 420, a humidity sensor 410, a pump 400, a variable airflow valve 390, a flow sensor 380, and last an atmospheric air valve 370, which provides the atmospheric air into the second valve 270, as well as discharging excess back into the atmosphere.

From the second valve 270, the patient sample 210/atmospheric air combination passes to a t-valve 280 which divides the patient sample 210/atmospheric air combination into two pathways. The first pathway leads from the valve 280 through a third valve 290, which further outlets to the atmosphere, and also outlets to a hydrogen sulfide storage coil 300. Valve 290 (optional) is preferably a pressure valve to provide proper volume of sample to H2S storage coil 300. Similarly, following the hydrogen sulfide coil 300 (optional), the patient sample 210/atmospheric air combination to a fourth valve 310 (optional pressure valve to provide proper sample volume to H2S storage coil 300), which divides the patient sample 210/atmospheric air, sending excess to the atmosphere, and the remainder to hydrogen sensor block 320 to test for hydrogen sulfide.

Also from the t-valve 280, the patient sample 210/atmospheric air combination is communicated through valve 330, which further outlets to the atmosphere, and also outlets to storage coil 340. In an alternative embodiment, unit 340 can be a molecular sieve column (separating column). Following the storage coil 340, the patient sample 210/atmospheric air is transmitted to a sixth valve 350, which divides the patient sample 210/atmospheric air combination, sending excess to the atmosphere, and the remainder to sensor block 360 which outlets to the atmosphere.

Sensor blocks 320 and 360 provide signals to a computer/display device, such as that disclosed in U.S. Pat. No. 9,140,685 incorporated herein by reference. The system is coupled to a computer/display unit at selected locations for monitoring and control, via connections preferably between for example the computer/display unit and: sample pumps 230, 400, humidity sensors 240/410, flow sensors 250/380, valves 260, 270, 310, 330, 370, and the hydrogen sulfide sensor block 320 and the second sensor block 360.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A breath testing apparatus comprising:
   a patient sample input for receiving exhaled breath from a patient;
   a hydrogen sulfide sensor block;
   a second sensor block coupled to at least one of a standard storage coil or a molecular sieve separating column;
   a first pathway from said patient sample input to a valve;
   a first pump between said patient sample input and said valve;
   a second pathway from said valve to said hydrogen sulfide sensor block;
   a third pathway from said valve to said standard storage coil or molecular sieve separating column, said third pathway further to said second sensor block; and
   the apparatus further comprising a second pump between an atmospheric input and said valve.

2. A breath testing apparatus according to claim 1, the apparatus further comprising a computer coupled to said hydrogen sulfide sensor block and said second sensor block.

3. A breath testing apparatus according to claim 1, the apparatus further comprising a first desiccation unit between said first pump and said patient sample input, and a second desiccation unit between said atmospheric input and said second pump.

4. A breath testing apparatus according to claim 1, the apparatus further comprising a first relief valve venting to the atmosphere between said patient sample input and said valve, and a second relief valve venting to the atmosphere between said atmospheric input and said valve.

5. A breath testing apparatus according to claim 1, the apparatus further comprising a first humidity sensor between said patient sample input and said valve.

6. A breath testing apparatus according to claim 1, said second sensor block comprising at least one of hydrogen, methane, and carbon dioxide sensors.

* * * * *